US010376693B2

(12) United States Patent
Yamazaki

(10) Patent No.: US 10,376,693 B2
(45) Date of Patent: Aug. 13, 2019

(54) HIGH-FREQUENCY COSMETIC TREATMENT APPARATUS

(71) Applicant: YA-MAN LTD., Tokyo (JP)

(72) Inventor: Iwao Yamazaki, Tokyo (JP)

(73) Assignee: YA-MAN LTD., Tokyo (JP)

( * ) Notice: Subject to any disclaimer, the term of this patent is extended or adjusted under 35 U.S.C. 154(b) by 340 days.

(21) Appl. No.: 14/958,118

(22) Filed: Dec. 3, 2015

(65) Prior Publication Data

US 2016/0089537 A1  Mar. 31, 2016

Related U.S. Application Data

(63) Continuation of application No. PCT/JP2014/002954, filed on Jun. 3, 2014.

(30) Foreign Application Priority Data

Jun. 4, 2013  (JP) ................................. 2013-117890

(51) Int. Cl.
*A61N 1/32* (2006.01)
*A61N 1/06* (2006.01)
(Continued)

(52) U.S. Cl.
CPC .............. *A61N 1/328* (2013.01); *A61B 18/14* (2013.01); *A61H 23/0245* (2013.01); *A61N 1/06* (2013.01);
(Continued)

(58) Field of Classification Search
CPC . A61N 1/328; A61N 1/06; A61N 7/00; A61H 23/0245; A61H 2201/0285;
(Continued)

(56) References Cited

U.S. PATENT DOCUMENTS 6,249,706 B1  6/2001 Sobota et al.
6,413,255 B1  7/2002 Stern
(Continued)

FOREIGN PATENT DOCUMENTS

CN  102985133  3/2013
JP  2002-537939  11/2002
(Continued)

OTHER PUBLICATIONS

International Preliminary Report on Patentability and Written Opinion issued by the International Bureau of WIPO dated Dec. 17, 2015, for International Application No. PCT/JP2014/002954.
(Continued)

*Primary Examiner* — Bo Joseph Peng
(74) *Attorney, Agent, or Firm* — Finnegan, Henderson, Farabow, Garrett & Dunner, L.L.P.

(57) ABSTRACT

A high-frequency cosmetic treatment apparatus capable of preventing local heating of a skin is provided. The high-frequency cosmetic treatment apparatus includes: a portable casing; side-by-side electrodes disposed at a tip portion of the casing with a predetermined interval provided therebetween, and having treatment surfaces to be contacted with a skin of a user; and a first power supply disposed in the casing, and to supply a high-frequency current to the pair of side-by-side electrodes.

11 Claims, 12 Drawing Sheets

(51) Int. Cl.
*A61B 18/14* (2006.01)
*A61H 23/02* (2006.01)
*A61N 7/00* (2006.01)
*A61B 18/00* (2006.01)
*A61B 90/00* (2016.01)

(52) U.S. Cl.
CPC .............. *A61B 2018/0047* (2013.01); *A61B 2018/00666* (2013.01); *A61B 2018/00708* (2013.01); *A61B 2018/00827* (2013.01); *A61B 2090/065* (2016.02); *A61H 2201/0214* (2013.01); *A61H 2201/0242* (2013.01); *A61H 2201/0285* (2013.01); *A61H 2201/10* (2013.01); *A61H 2201/50* (2013.01); *A61H 2201/5043* (2013.01); *A61H 2201/5058* (2013.01); *A61H 2201/5066* (2013.01); *A61H 2230/505* (2013.01); *A61N 7/00* (2013.01)

(58) Field of Classification Search
CPC .... A61H 2201/0242; A61H 2201/0214; A61H 2230/505; A61H 2201/5058; A61H 2201/5043; A61H 2201/5066; A61H 2201/50; A61H 2201/10; A61B 18/14; A61B 2090/065; A61B 2018/00827; A61B 2018/00708; A61B 2018/00666; A61B 2018/0047
See application file for complete search history.

(56) References Cited

U.S. PATENT DOCUMENTS

| | | | |
|---|---|---|---|
| 7,195,603 B2 * | 3/2007 | Yamazaki | A61H 23/0245 601/2 |
| 2006/0020309 A1 | 1/2006 | Altshuler et al. | |
| 2007/0106349 A1 | 5/2007 | Karni et al. | |
| 2007/0293918 A1 * | 12/2007 | Thompson | A61N 1/36021 607/72 |
| 2008/0312651 A1 * | 12/2008 | Pope | A61B 18/14 606/42 |
| 2009/0018628 A1 * | 1/2009 | Burns | A61B 18/14 607/101 |
| 2009/0171344 A1 * | 7/2009 | Pontis | A61B 18/1233 606/35 |
| 2010/0137752 A1 | 6/2010 | Heine et al. | |
| 2010/0211061 A1 * | 8/2010 | Leyh | A61B 18/1233 606/34 |
| 2011/0245735 A1 | 10/2011 | Eckhouse et al. | |
| 2013/0103119 A1 | 4/2013 | Yamanaka et al. | |

FOREIGN PATENT DOCUMENTS

| | | |
|---|---|---|
| JP | 2008-526421 | 7/2008 |
| JP | 2011-194173 | 10/2011 |
| JP | 2011-200307 | 10/2011 |
| JP | 2012-501784 | 1/2012 |
| JP | 2012-65693 | 4/2012 |
| KR | 10-2006-0103814 | 10/2006 |
| TW | 201300097 | 1/2013 |
| WO | WO 00/53113 | 9/2000 |
| WO | WO 2011/162174 | 12/2011 |

OTHER PUBLICATIONS

Notification of Reasons for Refusal issued by the Japanese Patent Office on Mar. 28, 2017, for Japanese application No. 2016-157930, and English-language translation thereof.
English-language International Search Report from the Japanese Patent Office for International Application No. PCT/JP2014/002954, dated Aug. 19, 2014.
Office Action from Japanese Patent Office in corresponding Japanese Patent Application No. 2015-521302, dated Jun. 26, 2018 (13 pages with English translation).

* cited by examiner

HIGH-FREQUENCY COSMETIC TREATMENT APPARATUS

CROSS-REFERENCE TO RELATED APPLICATIONS

This application is a continuation of prior International Application No. PCT/JP2014/002954 filed on Jun. 3, 2014, which is based upon and claims the benefit of priority from Japanese Patent Application No. 2013417890 filed on Jun. 4, 2013; the entire contents of all of which are incorporated herein by reference.

FIELD

Embodiments described herein relate generally to a high-frequency cosmetic treatment apparatus.

BACKGROUND

There has been conventionally known a high-frequency cosmetic treatment apparatus having a pair of spherical electrodes. In the high-frequency cosmetic treatment apparatus, it is possible to allow the pair of spherical electrodes to be brought into contact with a face, hands and feet and so on of a user to make a high-frequency current flow through a skin (dermis) positioned between the electrodes. This makes it possible to realize anti-aging of skin, healing of acne, and improvement of blotches, freckles, and the other skin troubles.

DETAILED DESCRIPTION

It is known that a high-frequency current flows by a shortest distance between electrodes on a skin surface. Specifically, the high-frequency current does not flow through the skin between spherical electrodes uniformly, but, the current flows intensively through the skin positioned on a straight line connecting a pair of spherical electrodes in a shortest distance.

The high-frequency current easily causes local heating of the skin, resulting in that the user sometimes feels uncomfortableness or gets burned.

The present invention is made by considering the above-described circumstances, and an object thereof is to provide a high-frequency cosmetic treatment apparatus capable of preventing local heating of a skin after being subjected to flow of a high-frequency current.

A high-frequency cosmetic treatment apparatus of an embodiment of the present invention includes: a portable casing; a pair of side-by-side electrodes to be contacted with a skin of a user, disposed at a tip portion of the casing, the pair of side-by-side electrodes contacting with a skin of a user to be treated; and a first power supply in the casing, and causing energization with a high-frequency current between the pair of side-by-side electrodes.

A high-frequency cosmetic treatment apparatus of an embodiment of the present invention can include: a portable casing; a heat sink in a tip portion of the casing; side-by-side electrodes disposed on the heat sink via a Peltier element, the pair of side-by-side electrodes contacting with a skin of a user to be treated; a first power supply in the casing, and supplying a high-frequency current between the side-by-side electrodes in pairs; and a second power supply in the casing, and supplying a drive current to the Peltier element.

It is also possible to configure such that the high-frequency cosmetic treatment apparatus of the embodiment of the present invention further includes a current sensor detecting a value of the high-frequency current which flows through the pair of side-by-side electrodes, in which the first power supply does not supply the high-frequency current to the pair of side-by-side electrodes when the value of the high-frequency current detected by the current sensor is equal to or greater than a threshold value.

It is also possible to configure such that the high-frequency cosmetic treatment apparatus of the embodiment of the present invention further includes a contact sensor detecting contact between the side-by-side electrodes and a skin surface, in which the first power supply supplies the high-frequency current to the pair of side-by-side electrodes in response to the detection of the contact between the pair of side-by-side electrodes and the skin surface detected by the contact sensor. Desirably, The pair of side-by-side electrodes includes electrodes which are arranged in parallel each other.

Hereinafter, embodiments will be described based on the drawings.

[First Embodiment]

Figure 1:
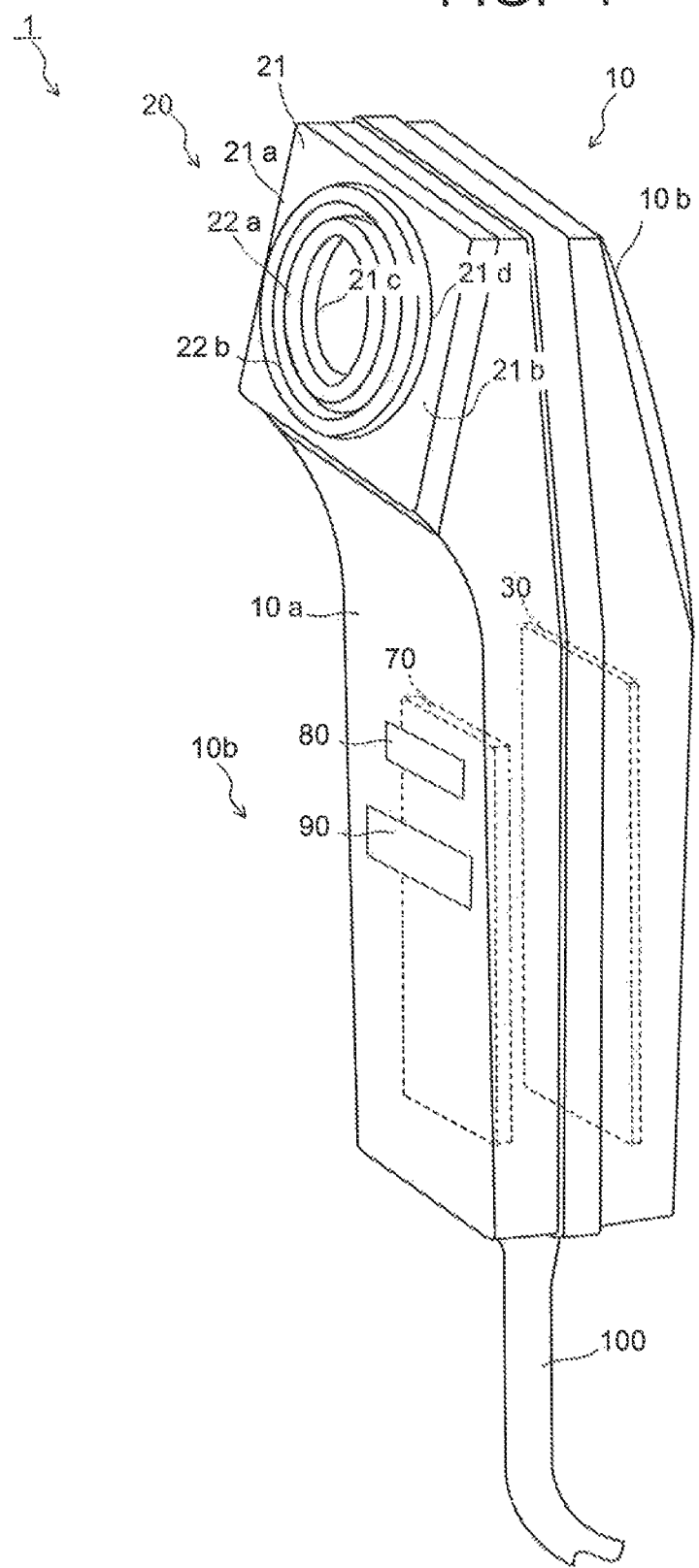
FIG. 1 is a perspective view illustrating a high-frequency cosmetic treatment apparatus 1 of a first embodiment.
Figure 2:
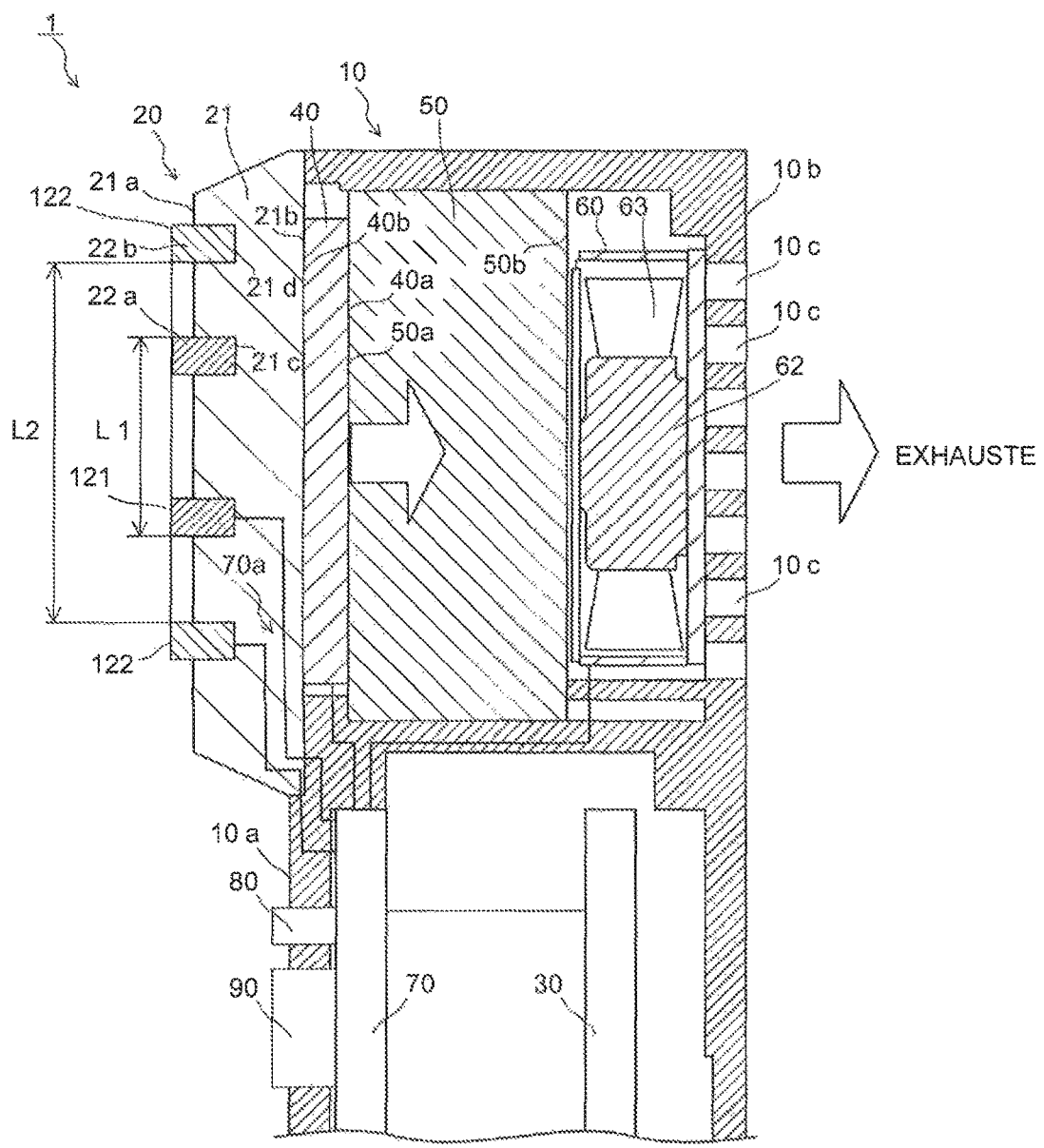
FIG. 2 is a partial sectional view of the high-frequency cosmetic treatment apparatus 1.

FIG. 1 is a perspective view illustrating a high-frequency cosmetic treatment apparatus 1. FIG. 2 is an enlarged sectional view illustrating a cross section of a part of the high-frequency cosmetic treatment apparatus 1 in an enlarged manner.

(Regarding High-frequency Cosmetic Treatment Apparatus 1)

As illustrated in FIG. 1 and FIG. 2, the high-frequency cosmetic treatment apparatus 1 of the first embodiment has a main body 10, and an electrode head 20. When a user who performs treatment makes the electrode head 20 abut against a skin surface of the user, it is possible to make a high-frequency current flow through the skin surface of the user. With the use of the high-frequency current, it is possible to perform cosmetic treatment on the skin of the user. Here, the "cosmetic treatment" means treatment in which the high-frequency current is used to realize anti-aging of skin, healing of acne, and improvement of blotches, freckles, and the other skin troubles.

(Regarding Main Body 10)

As illustrated in FIG. 2, the main body 10 houses a secondary battery 30, a Peltier element 40, a heat sink 50, a cooling fan 60, and a control circuit substrate 70 controlling these elements.

The main body 10 has an approximately rectangular parallelepiped shape. The main body 10 is formed by performing injection molding of plastic. The main body 10 is desirably formed of plastic being flame-resistant vinyl chloride resin, polyethylene, polycarbonate and the like.

The main body 10 has a front surface part 10a to which the electrode head 20 is attached, and a rear surface part 10b being a surface opposite to the front surface part 10a. A power cord 100 detachably attached to the main body 10. The power cord 100 connects a charging circuit of the secondary battery 30 to a commercial power supply (refer to FIG. 1).

An operation button 80 and a display part 90 are disposed at an approximately center portion of the front surface part 10a. The operation button 80 is operated by the user. The operation button 80 may be a touch-type switch displayed on a liquid crystal panel, or it may also be a mechanical switch. The display part 90 can include an LED or a liquid crystal display panel.

Exhaust holes 10c for exhausting air blown by the cooling fan 60 are provided on the rear surface part 10b at predetermined intervals.

(Regarding Electrode Head 20)

The electrode head 20 is formed of an electrode base 21, and a pair of electrodes 22a and 22b. The electrode base 21 can be formed by using various electrical insulating materials such as plastic, nonmetal, or ceramic. The electrode base 21 is formed to have a trapezoidal cross section. The electrode base 21 has a rectangular front surface 21a and a rectangular rear surface 21b. The electrode base 21 is attached to the main body 10 on a tip side thereof. Here, the rear surface 21b is closely brought into contact with the front surface part 10a of the main body 10. Each of the pair of electrodes 22a and 22b, the secondary battery 30, the Peltier element 40, the heat sink 50, and the cooling fan 60 is electrically connected to the control circuit substrate 70 by an electrical wiring 70a.

On the front surface 21a, there are formed circular ring-shaped inner groove portion 21c and outer groove portion 21d for holding the pair of electrodes 22a and 22b. Here, the inner groove portion 21c is formed to have a diameter smaller than that of the outer groove portion 21d.

The inner groove portion 21c and the outer groove portion 21d are arranged side-by-side in a circumferential direction. The description of "arranged side-by-side in the circumferential direction" means that a distance between the inner groove portion 21c and the outer groove portion 21d is approximately the same level at any position. Specifically, as illustrated in FIG. 2, the inner groove portion 21c is formed to have a diameter L1 including its outer peripheral edge smaller than a diameter L2 of an inner peripheral edge of the outer groove portion 21d. In brief, the inner groove portion 21c and the outer groove portion 21d are formed in a concentric, state, with a predetermined interval provided therebetween.

The electrode 22a is referred as a first electrode. The electrode 22a has a circular ring shape whose approximately center portion is opened. The electrode 22a is formed a planar electrode. The electrode 22a has a flat skin contact surface 121 which abuts against a skin surface of the user. The electrode 22a is attached to the inner groove portion 21c of the electrode base 21. A part of the electrode 22a including the skin contact surface 121 protrudes from the front surface of the electrode base 21.

The electrode 22b is referred as a second electrode. The electrode 22b is formed to have a circular ring shape whose approximately center portion is opened, in a similar manner to the electrode 22a. The electrode 22b is formed a planar electrode. The electrode 22b has a flat skin contact surface 122 which abuts against the skin surface of the user. The electrode 22b is attached to the outer groove portion 21d of the electrode base 21. The electrode 22b including the skin contact surface 122 protrudes from the front surface of the electrode base 21.

To the electrode 22a and the electrode 22b configured in the above-described manner, a high-frequency voltage of about 1 [MHz] to 4 [MHz] (high-frequency voltage of first frequency: RF voltage), for example, is applied by the control circuit substrate 70. Therefore, by making the electrode 22a and the electrode 22b abut against the skin surface of the user, it is possible to make the high-frequency current flow through the skin between the electrode 22a and the electrode 22b.

(Regarding Secondary Battery 30)

The secondary battery 30 is a standby power supply for supplying electric power to the pair of electrodes 22a and 22b, the Peltier element 40, the cooling fan 60, the control circuit substrate 70, and the like. The secondary battery 30 can be charged by a commercial power supply. By using the secondary battery 30, it is possible to use the high-frequency cosmetic treatment apparatus 1 in the outdoor environment or in the bath where it is difficult to obtain the electric power from the commercial power supply. The secondary battery 30 is, for example, a dry battery, a capacitor, or a fuel cell.

(Regarding Peltier Element 40)

The Peltier element 40 is a plate-shaped thermoelectric element formed by bonding different metals or semiconductors. The Peltier element 40 has a heat generating surface 40a and a heat absorbing surface 40b. The Peltier element 40 is disposed on the rear surface 21b side of the electrode head 20. The heat generating surface 40a is closely brought into contact with the heat sink 50. The heat absorbing surface 40b is adhered to the rear surface 21b of the electrode head 20.

When a current flows through a joint surface of the Peltier element 40, a thermal deviation occurs in the heat generating surface 40a and the heat absorbing surface 40b. Specifically, the heat generating surface 40a becomes hot, and the heat absorbing surface 40b becomes cold.

With this configuration, in the Peltier element 40, heat of the pair of electrodes 22.a and 22b, and the electrode base 21 of the electrode head 20 is transferred to the heat absorbing surface 40b. Consequently, it is possible to cool the entire electrode head 20 by using the Peltier element 40. Note that it is desirable to house the Peltier element 40 in the main body 10 so as to surround a periphery of the heat absorbing surface 40b with a heat insulating material. This makes it possible to prevent a temperature of the heat absorbing surface 40b rise due to the heat from the heat generating surface 40a through air around the Peltier element 40. (Regarding heat sink 50)

The heat sink 50 has an approximately rectangular parallelepiped shape. The heat sink 50 is formed of metal with good thermal conductivity (aluminum or copper, for example). The heat sink 50 has a sufficiently large thickness, when compared to a thickness of the electrode head 20 and a thickness of the Peltier element 40, and has a heat capacity larger than that of the electrode head 20 and that of the Peltier element 40. The heat sink 50 includes a flat surface 50*a* and a flat surface 50*b*. The heat sink 50 is thermally connected to the electrode head 20 via the Peltier element 40. The flat surface 50*a* is closely brought into contact with the heat generating surface 40*a* of the Peltier element 40. The flat surface 50*b* is closely brought into contact with the cooling fan 60.

Therefore, the heat of the heat generating surface 40*a* of the Peltier element 40 is efficiently transferred to the heat sink 50. Consequently, the heat of the electrode head 20 is efficiently transferred to the heat sink 50 via the Peltier element 40. Further, the heat transferred to the heat sink 50 is exhausted by the cooling fan 60 from the exhaust holes 10*c*. Although the illustration is omitted here, it is desirable to form a plurality of heat release fins on a surface portion of the heat sink 50. A contact area of the heat sink 50 with air is increased by the plurality of heat release fins, resulting in that efficiency of heat exhaustion performed by the cooling fan 60 is improved.

The cooling fan 60 is disposed in the vicinity of the exhaust holes 10*c*. The cooling fan 60 is a blower having a fan 63 which uses a shaft of a motor 62 as a rotation shaft.

(Regarding Control Circuit Substrate 70)

Figure 3:
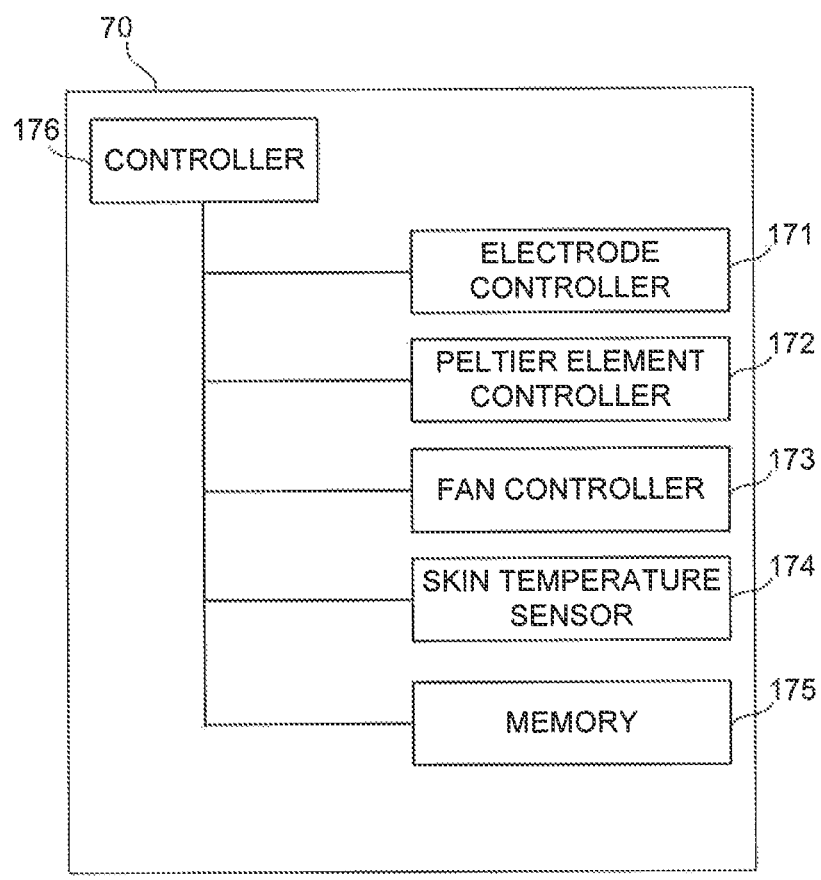
FIG. 3 is a block diagram illustrating functions of a control circuit substrate 70.

Next, the control circuit substrate 70 will be described by using FIG. 3. FIG. 3 is a functional block diagram of the control circuit substrate 70.

As illustrated in FIG. 3, the control circuit substrate 70 has an electrode controller 171, a Peltier element controller 172, a fan controller 173, a skin temperature sensor 174, a memory 175, and a controller 176 controlling these units. Each of the electrode controller 171 to the controller 176 is firmed of an electronic element (a capacitor, a coil, an IC chip, a memory, or the like, for example).

The electrode controller 171 is referred as a first power supply. The electrode controller 171 includes an oscillation circuit generating a high-frequency voltage applied to the pair of electrodes 22*a* and 22*b*, a boosting circuit boosting the oscillated voltage, and the like. The electrode controller 171 can apply a high-frequency voltage at a frequency from 1 [MHz] to 4 [MHz] to the pair of electrodes 22*a* and 22*b*.

The Peltier element controller 172 can apply a voltage to the Peltier element 40 to make a current flow through the element, to thereby drive the Peltier element. As a result of this, the heat generating surface 40*a* of the Peltier element 40 generates heat, and a temperature of the heat absorbing surface 40*b* is lowered. The Peltier element controller 172 can detect the temperature of the heat generating surface 40*a* or the heat absorbing surface 40*b* of the Peltier element 40 by using a sensor whose illustration is omitted. The Peltier element controller 172 can perform temperature control of the Peltier element 40 so that the temperature of the heat generating surface 40*a* or the heat absorbing surface 40*b* of the Peltier element 40 becomes approximately constant. For example, as the Peltier element controller 172 lowers a value of the voltage applied to the Peltier element 40, the temperature of the heat generating surface 40*a* of the Peltier element 40 decreases. If it is desired to increase the temperature of the heat generating surface 40*a* of the Peltier element 40, it is only required to increase the value of the voltage applied to the Peltier element 40.

It is also possible that the temperature of the heat generating surface 40*a* is kept constant by intermittently applying the voltage to the Peltier element 40.

The fan controller 173 drives the cooling fan 60. The fan controller 173 can detect temperatures of the electrode base 21 of the electrode head 20 and the heat generating surface 40*a* of the Peltier element 40 by using a sensor whose illustration is omitted. Further, the fan controller 173 can charge, based on the temperatures of the heat generating surface 40*a* and the electrode base 21 detected by the sensor, a rotation speed of the cooling fan 60 to set these temperatures to be equal to or less than a constant temperature.

In the above-described manner, the temperature control of the Peltier element 40 can be conducted by the Peltier element controller 172 and/or the fan controller 173 to set the temperature of the heat generating surface 40*a* or the heat absorbing surface 40*b* of the Peltier element 40 to be approximately constant.

The skin temperature sensor 174 functions as a current sensor. The skin temperature sensor 174 is electrically connected to the pair of electrodes 22*a* and 22*b*, and is an ammeter detecting a current which flows between the electrodes 22*a* and 22*b* in pairs.

When a high-frequency current flows through a skin of the user, the current generates heat on the skin, it is known that, at this time, an impedance inside the skin gradually decreases as a temperature of the skin increases. Therefore, an amount of current which flows between the electrodes 22*a* and 22*b* in pairs increases as the temperature of the skin increases.

The skin temperature sensor 174 converts the detected current into a numeric value indicating a skin temperature of the user. The skin temperature sensor 174 outputs the converted numeric value to the controller 176. Note that it is also possible to use an infrared detecting sensor as the skin temperature sensor 174.

In the memory 175, firmware required for the operation of the high-frequency cosmetic treatment apparatus 1, threshold values read by the Peltier element controller 172 and the fan controller 173, a threshold value which is compared with the numeric value indicating the skin temperature of the user output from the skin temperature sensor 174, and the like, are previously stored.

The controller 176 detects a press operation of the operation button 80 made by the user, to control the electrode controller 171 and the like. The controller 176 compares the numeric value indicating the skin temperature of the user output from the skin temperature sensor 174 with the threshold value read from the memory 175. When, as a result of the comparison, the numeric value indicating the skin temperature of the user is equal to or greater than the threshold value, the controller 176 controls the electrode controller 171 to stop the application of voltage to the pair of electrodes 22*a* and 22*b*. As a result of this, the flow of the high-frequency current flowing through the skin stops. This makes it possible to prevent the user from getting burned.

(Effect 1 Obtained by High-frequency Cosmetic Treatment Apparatus 1)

According to the high-frequency cosmetic treatment apparatus 1, when the user who performs treatment makes the pair of electrodes 22*a* and 22*b* abut against the skin of the user, it is possible to make the high-frequency current flow through the skin of the user. With this use of the high-frequency current, it becomes possible to realize anti-aging of skin, healing of acne, and improvement of blotches, freckles, and the other skin troubles.

At this time the entire electrode head 20 including the pair of electrodes 22*a* and 22*b* is cooled through heat exchange realized by the Peltier element 40.

Although a high-frequency current flow generates heat on the skin of the user, the entire electrode head 20 can be cooled by the Peltier element 40, so that, consequently, it is possible to remove heat inside the skin generated by the flow of the high-frequency current.

In detail, by cooling the electrode head 20 using the Peltier element 40, when the pair of electrodes 22a and 22b is brought into contact with the skin surface of the user by the user who performs treatment, it is possible to simultaneously cool the skin in the vicinity of the pair of electrodes 22a and 22b. As a result of this, the skin with heat generated by the flow of the high-frequency current via the pair of electrodes 22a and 22b can be immediately cooled by the electrode head 20 cooled by the Peltier element 40.

In brief, the Peltier element 40 and the electrode head 20 thermally connected to the Peltier element 40 function as a safety system for preventing the skin from being overheated by the high-frequency current flowing through the pair of electrodes 22a and 22b.

It is known that, when a high-frequency current flows through a skin surface, the inside of skin from the skin surface up to several [μm] to several [mm] is heated first. With the use of the high-frequency cosmetic treatment apparatus 1, the inside of the skin is gradually cooled from a superficial skin, by the electrode head 20 cooled by the Peltier element 40.

(Effect 2 Obtained by High-frequency Cosmetic Treatment Apparatus 1)

Figure 4:
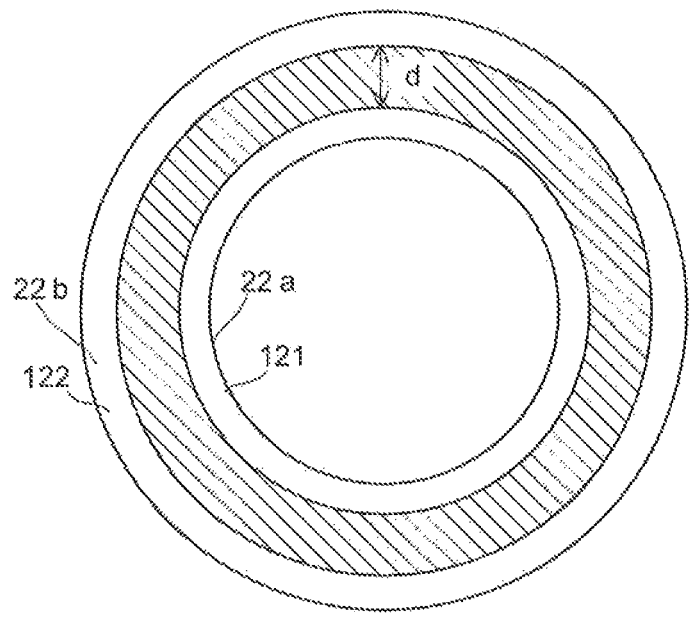
FIG. 4 is a view explaining a high-frequency current which flows through a pair of electrodes 22a and 22b.

Here, a further effect obtained by the high frequency cosmetic treatment apparatus 1 will be described in detail by using FIG. 4. FIG. 4 is a view explaining a high-frequency current which flows through the pair of electrodes 22a and 22b.

In the high-frequency cosmetic treatment apparatus 1 of this embodiment, the pair of electrodes 22a and 22b is mutually arranged side-by-side in a concentric state, as described above. Therefore, a distance d between the electrode 22a and the electrode 22.b becomes approximately the same level at any position. Consequently, the high-frequency current uniformly flows between the electrode 22a and the electrode 22b (refer to oblique lines in FIG. 4).

Accordingly, it becomes possible to make the high-frequency current flow through the user's skin between the electrode 22a and the electrode 22b uniformly in a wide range. By corresponding to this, a heat generating area of the skin of the user is also large, and stimulation caused by the energization is also applied uniformly. For example, a heating value per unit area of the skin becomes smaller than that in a case where the high-frequency current flowds between spherical electrodes. As a result of this, it is possible to prevent the conventional problem such that the skin is apt to locally generate heat due to the high-frequency current, and the user feels uncomfortableness.

(Effect 3 Obtained by High-frequency Cosmetic Treatment Apparatus 1)

Further, with the high-frequency cosmetic treatment apparatus 1, the skin contact surface 121 is flat. Therefore, a contact area of the electrode 22a and the skin surface of the user becomes wider than a contact area of the spherical electrode and the skin (the same applies to the electrode 22b). The spherical electrode does not have a flat skin contact surface As a result of this, when the pair of electrodes 22a and 22b are contacted with the skin surface of the user, it is possible to prevent uncomfortable feeling such as pricking feeling from being given to the user.

(Effect 4 Obtained by High-frequency Cosmetic Treatment Apparatus 1)

Further, with the use of the high-frequency cosmetic treatment apparatus 1, since the skin temperature sensor 174 is included, it is possible to monitor the skin temperature of the user. Therefore, it is possible to more securely prevent the user from getting burned.

[Second Embodiment]

Next, a high-frequency cosmetic treatment apparatus 2 of a second embodiment of the present invention will be described by using FIG. 5 to FIG. 8.

Figure 5:
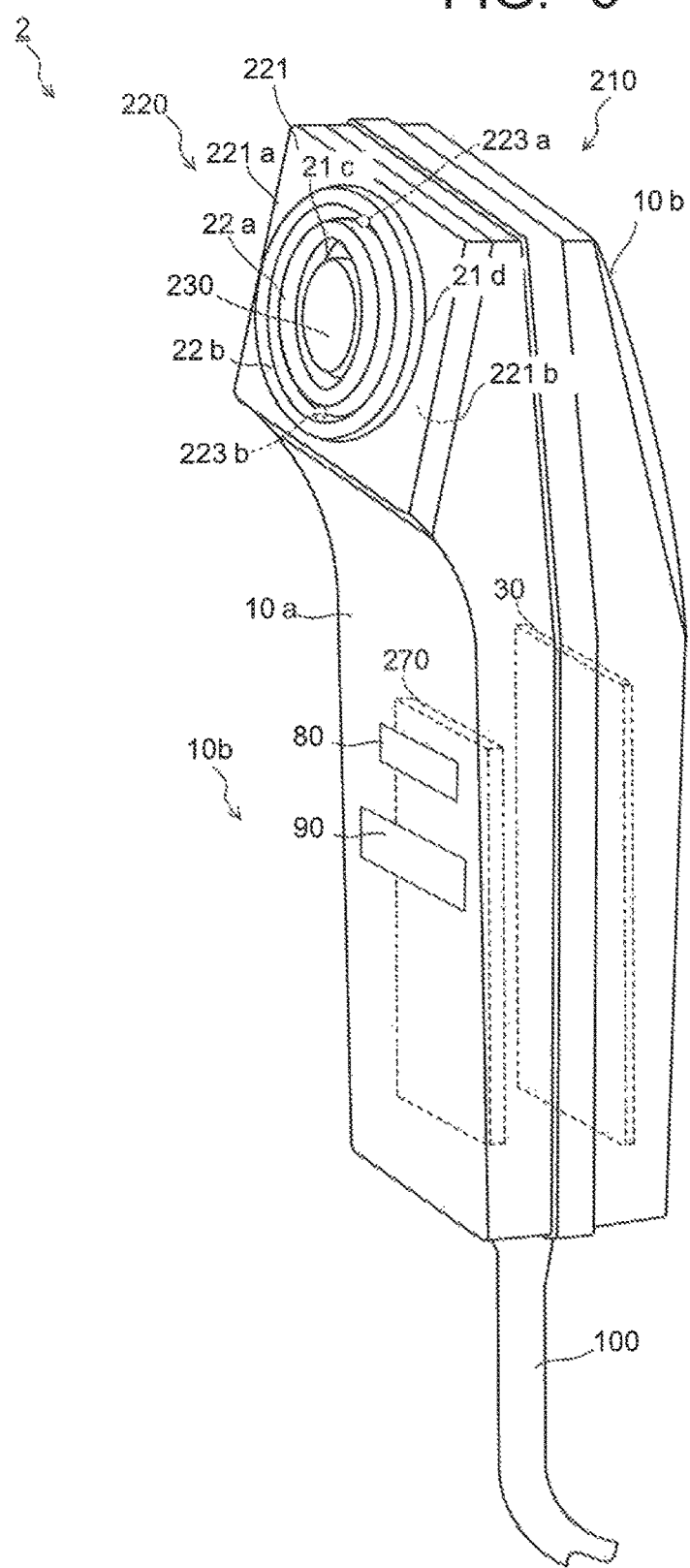
FIG. 5 is a perspective view illustrating a high-frequency cosmetic treatment apparatus 2 of a second embodiment.
Figure 6:
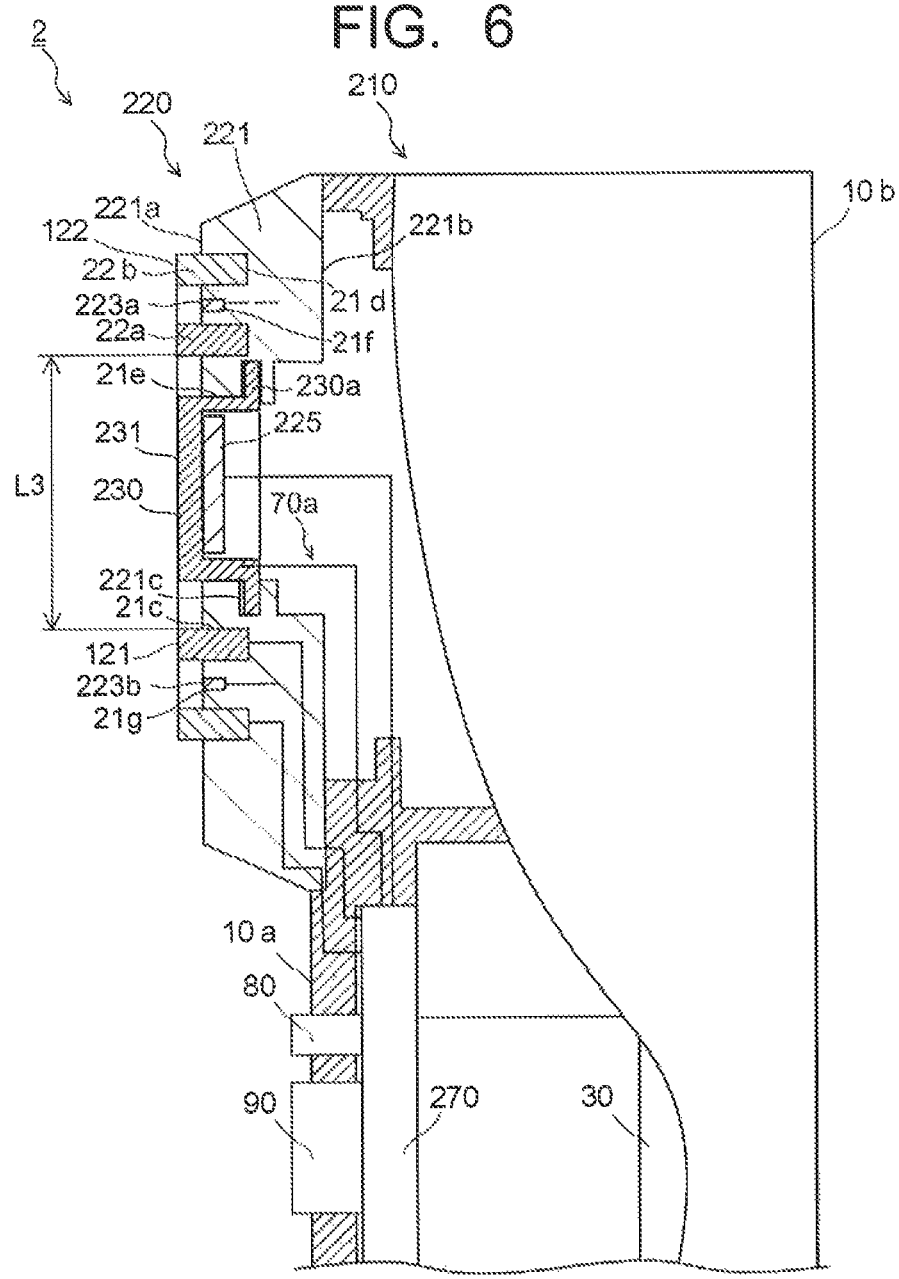
FIG. 6 is a partial sectional view of the high-frequency cosmetic treatment apparatus 2.
Figure 7:
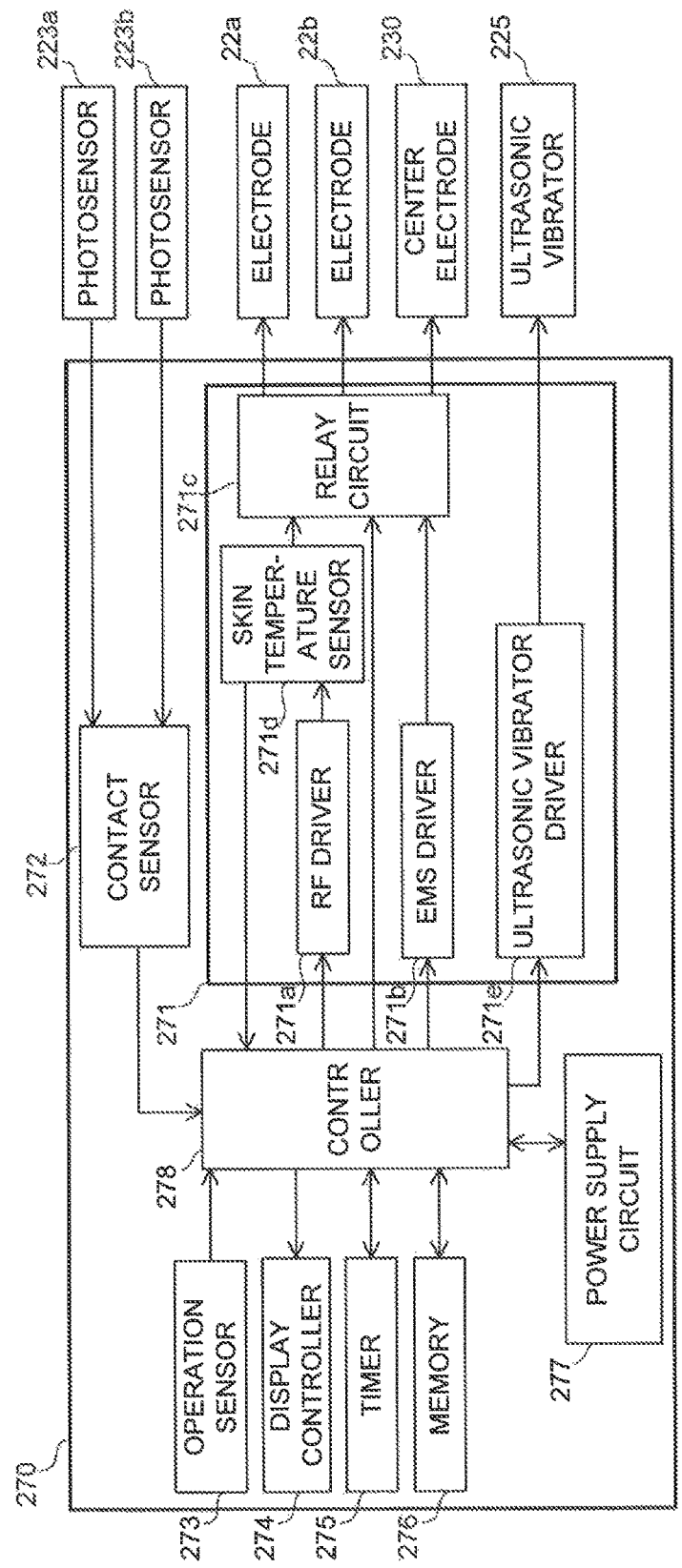
FIG. 7 is a block diagram illustrating functions of a control circuit substrate 270.

First, a configuration of the high-frequency cosmetic treatment apparatus 2 will be described by using FIG. 5 to FIG. 7. FIG. 5 is a perspective view illustrating the high-frequency cosmetic treatment apparatus 2. FIG. 6 is an enlarged sectional view illustrating a cross section of a part of the high-frequency cosmetic treatment apparatus 2 in an enlarged manner. FIG. 7 is a block diagram explaining functions of the high-frequency cosmetic treatment apparatus 2. Hereinafter, parts corresponding to those of the high-frequency cosmetic treatment apparatus 1 of the first embodiment will be denoted by the same reference numerals, and detailed explanation thereof will be omitted.

As illustrated in FIG. 5 and FIG. 6, the high-frequency cosmetic treatment apparatus 2 includes a main body 210, an electrode head 220, a photosensor 223a, a photosensor 223b, an ultrasonic vibrator 225, and a control circuit substrate 270.

The main body 210 has a shape and a structure corresponding to those of the main body 10 included by the high-frequency cosmetic treatment apparatus 1. However, the main body 210 does not house the Peltier element 40, the heat sink 50, and the cooling fan 60. Therefore, the exhaust holes 10c are not formed on the main body 210.

The electrode head 220 has a shape, a structure, and a function corresponding to those of the electrode head 20. The electrode head 220 is formed of an electrode base 221, the pair of electrodes 22a and 22b, and a center electrode 230.

Each of the pair of electrodes 22a and 22b, the center electrode 230, the photosensor 223a, the photosensor 223b, and the ultrasonic vibrator 225 is electrically connected to the control circuit substrate 270 by the electrical wiring 70a.

The electrode base 221 has a rectangular front surface 221a and a rectangular rear surface 221b. On the front surface 221a, there are formed circular ring-shaped inner groove portion 21c, outer groove portion 21d, and center hole 21e for respectively holding the pair of electrodes 22a and 22b, and the center electrode 230. A sensor attachment hole 21f and a sensor attachment hole 21g are formed on the front surface 221a.

The center hole 21e is formed to have an approximately perfect circular shape. The center hole 21e is positioned at a center portion of the electrode base 221. The center hole 21e is provided from the front surface 221a to the rear surface 221b. The center hole 21e is arranged in a concentric state with the inner groove portion 21c and the outer groove portion 21d. A circumferential portion of the center hole 21e is arranged side-by-side with a circumferential portion of the inner groove portion 21c. An interval between the circumferential portion of the center hole 21e and the circumferential portion of the inner groove portion 21c becomes approximately the same level at any position, in a similar manner to the distance d in FIG. 4. The center electrode 230 is inserted into the center hole 21e.

Each of the sensor attachment hole 21f and the sensor attachment hole 21g is arranged between the inner groove portion 21c and the outer groove portion 21d. The sensor attachment hole 21f and the sensor attachment hole 21g are arranged so as to sandwich the center hole 21e, in a longitudinal direction of the main body 210. The photosensor 223a is inserted into the sensor attachment hole 21f. The photosensor 223b is inserted into the sensor attachment hole 21g.

The center electrode 230 is referred as a third electrode. The inside of the center electrode 230 is hollow and has an approximately columnar shape. The center electrode 230 has a shape corresponding to that of the center hole 21e. The center electrode 230 can be formed of metal. It is also possible to use a thin metal plate for the center electrode 230.

The center electrode 230 is adhered to the ultrasonic vibrator 5. Vibration is given to the center electrode 230 from the ultrasonic vibrator 225, and the center electrode 230 vibrates together with the ultrasonic vibrator 225.

The center electrode 230 includes flange portions 230a. When the flange portions 230a are disposed in recessed portions 221c inside the electrode base 221, the center electrode 230 can be prevented from falling off the center hole 21e.

The center electrode 230 is smaller than an inside diameter L3 of the electrode 22b. A peripheral edge of the center electrode 230 is arranged side-by-side with a peripheral edge of the electrode 22a.

The center electrode 230 has a skin contact surface 231. The skin contact surface 231 is contacted with a skin surface of the user. The skin contact surface 231 is formed in a flat shape. The skin contact surface 231 can also be formed in a curved surface shape. By forming the skin contact surface 231 in the curved surface shape, it becomes easy to make the skin contact surface 231 abut against a curved surface of the skin of the user. As a result of this, it is possible to increase an abutting area between the skin of the user and the skin contact surface 231.

A part of the center electrode 230 including the skin contact surface 231 protrudes from the front surface 221a.

To the center electrode 230 and the electrode 22b, a voltage from 5 [Hz] to 100 [kHz] (voltage of second frequency; EMS voltage), for example, is applied by the control circuit substrate 270. The EMS voltage is a voltage from low to medium frequency. The EMS (Electrical Muscle Stimulation) means that muscles are electrified to forcibly contract the muscles. The contracted muscles return to their original states at a point of time at which a value of the EMS voltage is 0. By repeating this operation, it is possible to realize muscle-building. Note that it is also possible to apply the EMS voltage between the center electrode 230 and the electrode 22a. It is also possible to apply the EMS voltage between the electrode 22a and the electrode 22b.

The photosensor 223a is a first contact sensor. The photosensor 223b is a second contact sensor. The photosensor 223a and the photosensor 223b detect the contact of the pair of electrodes 22a and 22b, and the center electrode 230 with respect to the skin surface of the user. Each of the photosensor 223a and the photosensor 223b is a photodiode, for example. Each of the photosensor 223a and the photosensor 223b outputs a current with a magnitude corresponding to illuminance in a periphery thereof to the control circuit substrate 270.

The ultrasonic vibrator 225 vibrates in a thickness direction when a voltage is applied thereto. At this time, the center electrode 230 adhered to the ultrasonic vibrator 225 vibrates, in synchronization with the vibration of the ultrasonic vibrator 225.

The vibration of the ultrasonic vibrator 225 also propagates to the electrode base 221. Specifically, the entire electrode base 221 vibrates due to the vibration of the ultrasonic vibrator 225. It is possible to give a massage effect provided by the vibration to the skin of the user.

For example, it is also possible to design such that only the center electrode 230 is vibrated by interposing a rubber cushion between the center electrode 230 and the electrode base 221, or by providing space between the center electrode 230 and the electrode base 221.

The above is the description regarding the main configuration of the high-frequency cosmetic treatment apparatus 2.

Here, patterns of application of voltage to the respective components (the pair of electrodes 22a and 22b, the center electrode 230, and the ultrasonic vibrator 225) will be described. The high-frequency cosmetic treatment apparatus 2 has application patterns of voltage as described in the following 1 to 7 (referred to as operation patterns [1] to [7], hereinafter). It is possible to make a current flow through the skin of the user with the use of the operation patterns [1] to [6]. It is possible to apply stimulation of vibration to the skin of the user with the use of the operation pattern [7].

[1] RF mode 1: The RF voltage is applied to the pair of electrodes 22a and 22b.

[2] RF mode 2: The RF voltage is applied between the electrode 22b and the center electrode 230.

[3] RF mode 3: The RF voltage is applied between the electrode 22a and the center electrode 230.

[4] EMS mode 1: The EMS voltage is applied to the pair of electrodes 22a and 22b.

[5] EMS mode 2: The EMS voltage is applied between the electrode 22b and the center electrode 230.

[6] EMS mode 3: The EMS voltage is applied between the electrode 22a and the center electrode 230.

[7] Vibration mode: The ultrasonic vibrator 225 vibrates.

In the high-frequency cosmetic treatment apparatus 2, the above-described operation patterns [1] to [7] can be carried out in order every predetermined time. In the high-frequency cosmetic treatment apparatus 2, an operating time can be set for each of the above-described operation patterns [1] to [7]. This operating time can be appropriately changed.

In the high-frequency cosmetic treatment apparatus 2, it is possible to carry out the above-described operation patterns [1] to [7] by combining the patterns in an appropriate manner. Specifically, there is a case where any operation out of the above-described operation patterns [1] to [7] is not conducted by the high-frequency cosmetic treatment apparatus 2.

In the high-frequency cosmetic treatment apparatus 2, the operation pattern [7] can also be conducted simultaneously with the other operation patterns [1] to [6].

In the high-frequency cosmetic treatment apparatus 2, it is possible to change intensity (level) of the voltage applied to the respective components (the pair of electrodes 22a and 22b, the center electrode 230, and the ultrasonic vibrator 225) in the above-described operation patterns [1] to [7]. For example, in the high-frequency cosmetic treatment apparatus 2, the intensity of the voltage can be changed in five stages of level (weak) to level 5 (strong), for each of the components.

(Regarding Control Circuit Substrate 270)

ON or OFF of the execution of the above-described operation patterns [1] to [7], and the change in the level of the voltage are controlled by respective electronic circuits formed on the control circuit substrate 270.

As illustrated in FIG. 7, the control circuit substrate 270 has an electrode controller 271, a contact sensor 272, an operation sensor 273, a display controller 274, a timer 275, a memory 276, a power supply circuit 277, and a controller 278 controlling these units.

Each of the electrode controller 271 to the controller 278 is formed of an electronic element (a capacitor, a coil, an IC chip, or the like, for example).

The electrode controller 271 includes an RF driver 271a, an EMS driver 271b, a relay circuit 271c, a skin temperature sensor 271d, and an ultrasonic vibrator driver 271e. The electrode controller 271 has a function corresponding to that of the electrode controller 171. The RF driver 271a functions as first and third power supplies. The RF driver 271a functions as a vibration controller.

The RF driver 271a includes an oscillation circuit having a DC-AC converting function and generating the RF voltage, a boosting circuit boosting the voltage, and the like. The RF driver 271a receives, from the controller 278, a signal indicating intensity of the RF voltage generated by the RF driver 271a (RF voltage control signal). Here, the intensity of the RF voltage generated by the RF driver 271a is represented by level 1 to level 5. The RF voltage control signal is a signal indicating the level 1 to level 5. A value indicating the intensity of the RF voltage generated by the RF driver 271a is previously held in the memory 276.

The RF driver 271a performs, in response to the voltage control signal received from the controller 278, DC-AC conversion on a direct-current voltage of 5 [V] input from the power supply circuit 277, and boosts the voltage in a range of 60 to 150 [V]. Note that a value of the boosted voltage indicated here is Peak-to-Peak-Value. For example, an alternating voltage of 60 [V] indicated here is an alternating voltage whose maximum value is from +30 [V] to −30 [V]. By this voltage, intensity of a current which flows through the skin of the user changes. The RF driver 271a applies the RF voltage to the electrode 22a, the electrode 22b, or the center electrode 230 via the relay circuit 271c.

The EMS driver 271b includes an oscillation circuit having a DC-AC converting function and generating the EMS voltage, a boosting circuit boosting the voltage, and the like. The EMS driver 271b receives, from the controller 278, a signal indicating intensity of the EMS voltage generated by the EMS driver 271b (EMS voltage control signal). Here, the intensity of the EMS voltage generated by the EMS driver 271b is represented by level 1 to level 5. The EMS voltage control signal is a signal indicating the level 1 to level 5. A value indicating the intensity of the EMS voltage is previously held in the memory 276.

The EMS driver 271b performs, in response to the voltage control signal received from the controller 278, DC-AC conversion on a direct-current voltage of 5 [V] input from the power supply circuit 277, and boosts the voltage in a range of 10 to 150 [V]. Note that a value of the boosted voltage indicated here is Peak-to-Peak-Value. For example, an alternating voltage of 60 [V] indicated here is an alternating voltage whose maximum value is from +30 [V] to −30 [V]. By this voltage, the intensity of the current which flows through the skin of the user changes. The EMS driver 271b applies the EMS voltage to the electrode 22a, the electrode 22b, or the center electrode 230 via the relay circuit 271c.

The relay circuit 271c configured by a transistor, a capacitor and the like. The relay circuit 271c is controlled by the controller 278 to switch patterns regarding the electrodes (the electrode 22a, the electrode 22b, or the center electrode 230) connected to the RF driver 271a.

(Pattern 1)

The relay circuit 271c connects the electrode 22a and the electrode 22b to the RF driver 271a. As a result of this, the RF voltage is applied between the electrode 22a and the electrode 22b by the RF driver 271a. At this time, the center electrode 230 is in a state of being electrically insulated from the electrode 22a and the electrode 22b.

(Pattern 2)

The relay circuit 271c connects the electrode 22a and the center electrode 230 to the RF driver 271a. As a result of this, the RF voltage is applied between the electrode 22a and the center electrode 230 by the RF driver 271a. At this time, the electrode 22b is electrically insulated from the electrode 22a and the center electrode 230.

(Pattern 3)

The relay circuit 271c connects the electrode 22b and the center electrode 230 to the RF driver 271a. As a result of this, the RF voltage is applied between the electrode 22b and the center electrode 230 by the RF driver 271a. At this time, the electrode 22a is electrically insulated from the electrode 22b and the center electrode 230.

In a similar manner, the relay circuit 271c is controlled by the controller 278 to switch patterns regarding the electrodes (the electrode 22a, the electrode 22b, or the center electrode 230) connected to the EMS driver 271b. When the EMS driver 271b, and the electrode 22a, the electrode 22b, or the center electrode 230 are connected, the RF driver 271a, and the electrode 22a, the electrode 22b, or the center electrode 230 are electrically insulated.

The skin temperature sensor 271d has a function corresponding to that of the skin temperature sensor 174. The skin temperature sensor 271d functions as a current sensor. The skin temperature sensor 271d detects a value of a current flowed through the skin of the user by the driving of the RF driver 271a. The skin temperature sensor 271d converts the detected value of the current into a numeric value indicating a skin temperature of the user, and outputs the numeric value to the controller 278.

The ultrasonic vibrator driver 271e can output a high-frequency voltage at a frequency from 40 [kHz] to 4 [MHz] to the ultrasonic vibrator 225. The high-frequency voltage output by the ultrasonic vibrator driver 271e is previously set in accordance with a natural frequency of the ultrasonic vibrator 225.

The ultrasonic vibrator driver 271e is controlled by the controller 278 to apply the high-frequency voltage to the ultrasonic vibrator 225. The ultrasonic vibrator driver 271e includes an oscillation circuit having a DC-AC converting function and generating the high-frequency voltage, a boosting circuit boosting the voltage, and the like. For example, the ultrasonic vibrator driver 271e can perform DC-AC conversion on a direct-current voltage of 5 [V] input from the power supply circuit 277, and boost the voltage up to 24 [V]. Note that a value of the boosted voltage indicated here is Peak-to-Peak-Value. Specifically, an alternating voltage of 24 [V] indicated here is an alternating voltage whose maximum value is from +12 [V] to −12 [V].

The contact sensor 272 constantly monitors outputs of the photosensor 223a and the photosensor 223b. To the contact sensor 272, currents output by the photosensor 221a and the photosensor 223b are input.

The contact sensor 272 compares the predetermined threshold value and the input currents. When the current input from the photosensor 223a is smaller than the threshold value, the contact sensor 272 outputs a first contact detection signal to the controller 278.

When the current input from the photosensor 223b is smaller than the threshold value, the contact sensor 272 outputs a second contact detection signal to the controller 278. Further, when the photosensor 223a does not output a current, the contact sensor 272 treats a current from the photosensor 223a as 0 [mA]. In like manner, when the photosensor 223*b* does not output a current, the contact sensor 272 treats a current from the photosensor 223*b* as 0 [mA].

Note that it is also possible that the contact sensor 272 outputs the first and second contact detection signals to the controller 278 based on values of voltages of signals output by the photosensor 223*a* and the photosensor 223*b*. Further, it is also possible that the contact sensor 272 outputs the first or second contact detection signal to the controller 278 based on whether or not the current is input from the photosensor 223*a* or the photosensor 223*b*.

The operation sensor 273 detects the press operation of the operation button 80. The "press operation" corresponds to, for example, ON or OFF of main power supply. The operation sensor 273 also accepts an operation of indicating switching of the operation of the high-frequency cosmetic treatment apparatus 2, and an operation for setting the operating time of the high-frequency cosmetic treatment apparatus 2. The operation sensor 273 also accepts an operation of changing the level of the voltage.

The display controller 274 controls the display part 90. When the display part 90 is formed of the LED, for example, the display controller 274 controls light emission of the LED. When the display part 90 includes a liquid crystal display, for example, the display controller 274 outputs an image signal to the liquid crystal display.

The timer 275 is controlled by the controller 278 to measure time. In accordance with the time measured by the timer 275, the operation patterns [1] to [7] of the high-frequency cosmetic treatment apparatus 2 are switched in order, or the main power supply is turned OFF after a given length of time elapses.

The memory 276 previously stores the firmware required for the operation of the high-frequency cosmetic treatment apparatus 2, the various threshold values, the information indicating the levels of the voltages, the information regarding the time to be measured by the timer 275.

It is also possible to make the memory 276 previously store the values of the voltages of the signals output by the RF driver 271*a*, the EMS driver 271*b*, the skin temperature sensor 271*d*, and the ultrasonic vibrator driver 271*e*. It is also possible to make the memory 276 previously store the information indicating the patterns of the electrodes connected by the relay circuit 271*c*.

On the power supply circuit 277, there are formed the charging circuit of the secondary battery 30, an electric contact to which the power cord 100 can be attached/detached, and the like. It is also possible to provide a boosting circuit to the power supply circuit 277. In this case, there is no need to provide the boosting circuit in the RF driver 271*a* and the like.

The controller 278 has a function corresponding to that of the controller 176. The controller 278 controls the electrode controller 271 based on the press operation of the operation button 80 detected by the operation sensor 273.

The controller 278 controls, based on the numeric value indicating the skin temperature of the user output by the skin temperature sensor 271*d*, the RF driver 271*a* so as to change the level of the voltage. The controller 278 controls, based on the first or second contact detection signal output by the contact sensor 272, the RF driver 271*a* or the EMS driver 271*b* so as to change the level of the voltage.

(Explanation of Operation)

Figure 8:
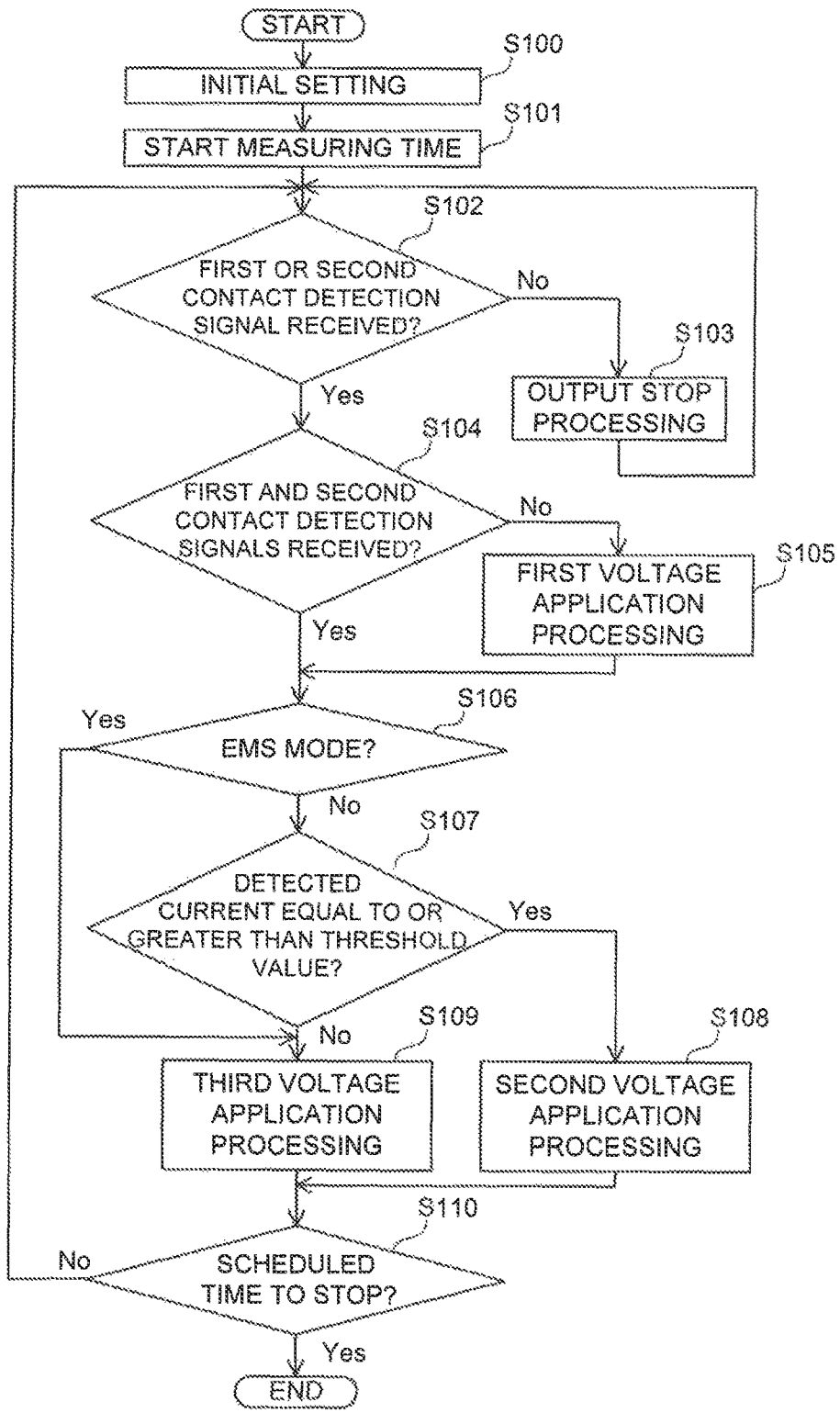
FIG. 8 is a flow chart illustrating an operation of the high-frequency cosmetic treatment apparatus 2.

Next, the operation of the high-frequency cosmetic treatment apparatus 2 will be described by using FIG. 8. FIG. 8 is a flow chart illustrating the operation of the high-frequency cosmetic treatment apparatus 2.

(1) Initial Setting (Step S100)

For example, when the press operation of the operation button 80 is performed, the main power supply is turned ON. At this time, there is a case where the high-frequency cosmetic treatment apparatus 2 automatically operates in the order of the operation pattern [2] RF mode 2, the operation pattern [7] vibration mode, and the operation pattern [5] EMS mode 2.

In this case, the controller 278 first reads the RF voltage control value, a drive time of the operation pattern [2] RF mode 2, or the like, as an initial value, from the memory 276. Here, it is set that the RF voltage control value indicating the level 3 is read as the initial value, as an example.

(2) Start Measuring Time (Step S101)

The controller 278 controls the timer 275 to make the timer 275 measure the read drive time of the operation pattern [2] RF mode 2.

(3) Output Stop Processing (No in Step S102, S103)

There is a case where currents output by the photosensor 223*a* and the photosensor 223*b* are equal to or greater than the threshold value. For example, the above case corresponds to a case where the electrode head 220 is not brought into contact with the skin surface of the user. For example, the above case corresponds to a case where the electrode head 220 is slightly brought into contact with the skin surface of the user.

In such a case, the contact sensor 272 does not output the first and second contact detection signals to the controller 278 (No in step S102). Therefore, the controller 278 does not drive the RF driver 271*a*. When the RF driver 271*a* is already driven, the controller 278 stops the RF driver 271*a*.

As a result of this, the application of the RF voltage between the electrode 22*b* and the center electrode 230 is stopped (step S103).

(4) Contact 1 of Electrode Head 220 (Yes in Step S102 to S105)

There is a case where the current output by either the photosensor 223*a* or the photosensor 223*b* is equal to or less than the threshold value. For example, the above case corresponds to a case where an upper side or a lower side a the electrode head 220 is brought into contact with the skin surface of the user.

In this case, the contact sensor 272 outputs either the first or second contact detection signal to the controller 278 (Yes in step S102, No in step S104)

The controller 278 reads the value indicating the level 1, as the value indicating the intensity of the RF voltage, from the memory 276, and outputs the RF voltage control signal to the RF driver 271*a*. As a result of this, the RF driver 271*a* generates the weakest RF voltage. The RF voltage of the level 1 is applied between the electrode 22*b* and the center electrode 230 (step S105: first application processing). Consequently, the RF current flows through the skin surface of the user based on the RF voltage of the level 1.

Note that it is also possible that the controller 278 outputs the signal indicating the level 2 to the RF driver 271*a*.

(5) Contact 2 of Electrode Head 220 (Yes in Step S104)

There is a case where the currents output by both of the photosensor 223*a* and the photosensor 223*b* are equal to or less than the threshold value. For example, the above case corresponds to a case where the entire electrode head 220 is closely brought into contact with the skin surface of the user. In this case, the contact sensor 272 outputs the first and second contact detection signals to the controller 278 (Yes in step S104).

(6) Skin temperature detection processing (No in step S106 to S108)

When the operation pattern [2] RF mode 2 is performed (No in step S106), the controller 278 compares the numeric value indicating the skin temperature of the user output by the skin temperature sensor 271d, and the threshold value held in the memory 276 (step S107).

(7) Second Voltage Application Processing (Yes in Step S107, S108)

There is a case where the numeric value indicating the skin temperature of the user output by the skin temperature sensor 271d is equal to or greater than the threshold value (Yes in step S107). In this case, the controller 278 controls the RF driver 271a so that a voltage of a level which is weaker by one stage than the level read in step S100 is applied between the electrode 22b and the center electrode 230.

Here, the controller 278 outputs the signal indicating the level 2, which is weaker by one stage than the level 3, to the RF driver 271a. As a result of this, the RF driver 271a generates the second-weakest RF voltage. Therefore, the RF voltage of the level 2 is applied between the electrode 22b and the center electrode 230 (step S108: second application processing).

As a result of this, the RF current flows through the skin surface of the user based on the RF voltage of the level 2. Note that there is a case where the instruction of setting the intensity of the high-frequency voltage to the level 5, is already accepted by the operation sensor 273 during a period from steps S100 to S107. In this case, the controller 278 outputs, in step S108, the signal indicating the level 4 which is lower by one stage than the level 5, to the RF driver 271a.

(8) Third Voltage Application Processing (No in Step S107, S109)

There is a case where the numeric value indicating the skin temperature of the user output by the skin temperature sensor 271d is lower than the threshold value (No in step S107). In this case, the controller 278 outputs the value indicating the level read in step S100 to the RF driver 271a as the RF voltage control signal.

Here, the controller 278 outputs the signal indicating the level 3. As a result of this, the RF driver 271a generates the RF voltage corresponding to the level 3. Therefore, the RF voltage of the level 3 is applied between the electrode 22b and the center electrode 230 (step S109: third application processing).

As a result of this, the RF current flows through the skin surface of the user based on the RF voltage of the level 3. Note that there is a case where the instruction of setting the intensity of the high-frequency voltage to the level 5, is already accepted by the operation sensor 273 during the period from steps S100 to S107. In this case, the controller 278 outputs, in step S109, the signal indicating the level 5 to the RF driver 271a.

(9) Case of EMS Mode (Yes in Step S106, and Step S109)

There is a case where the operation pattern is the [5] EMS mode 2. It is often the case where, when the EMS voltage is applied to the skin surface, the temperature of the skin surface does not increase, when compared to a case where the RF voltage is applied. Therefore, when the operation pattern is the [5] EMS mode 2, the controller 278 executes step S109.

(10) Repetitive Processing (Step S110)

The controller 278 repeatedly executes steps S102 to S109 during a period of the operation pattern [2] RF mode 2. When the lapse of predetermined time is confirmed by the timer 275 (Yes in step S110), the controller 278 switches the operation mode of the high-frequency cosmetic treatment apparatus 2 in the order of the operation pattern [7], and the operation pattern [5] EMS mode 2, while repeatedly conducting steps S101 to S110.

For example, when the high-frequency cosmetic treatment apparatus 2 operates in the [5] EMS mode 2, the controller 278 reads the value indicating the intensity of the EMS voltage, and the like, from the memory 276.

(Effect 1 Obtained by High-frequency Cosmetic Treatment Apparatus 2)

With the use of the high-frequency cosmetic treatment apparatus 2, it is possible to obtain an effect corresponding to that of the high-frequency cosmetic treatment apparatus 1. With the use of the high-frequency cosmetic treatment apparatus 2, since the center electrode 230 is provided, the contact area between the electrode and the skin surface of the user can be increased. Consequently, the amount of current which flows through the skin per unit area of the user becomes small, which enables to easily reduce the stimulation sensed when the EMS voltage is applied to the skin.

(Effect 2 Obtained by High-frequency Cosmetic Treatment Apparatus 2)

With the use of the high-frequency cosmetic treatment apparatus 2, it is possible to automatically switch the different operation patterns in order. Specifically, it is possible to sequentially apply different stimulations to the skin surface of the user. Consequently, the user is difficult to get bored with the use of the high-frequency cosmetic treatment apparatus 2, and it is possible to efficiently use the high-frequency cosmetic treatment apparatus 2.

(Effect 3 Obtained by High-frequency Cosmetic Treatment Apparatus 2)

In the high-frequency cosmetic treatment apparatus 2, the RF driver 271a is driven when the electrode head 220 is surely brought into contact with the skin surface of the user, which enables to improve the safety.

(Effect 4 Obtained by High-frequency Cosmetic Treatment Apparatus 2)

In the high-frequency cosmetic treatment apparatus 2, it is possible to change the intensity of the voltage applied to the electrode 22b, the center electrode 230, and the like, in accordance with the outputs of the photosensor 223a and the photosensor 223b. For example, if the contact area between the user and the electrode 22b is very small, the user often feels uncomfortableness when a strong voltage is applied to the skin surface of the user.

In the high-frequency cosmetic treatment apparatus 2, since the voltage applied to the electrode 22b, the center electrode 230, and the like can be weakened, it is possible to prevent the user from feeling uncomfortableness.

(Effect 5 Obtained by High-frequency Cosmetic Treatment Apparatus 2)

For example, there is a case where the high-frequency cosmetic treatment apparatus 2 is operated in the operation pattern [1] RF mode 1. When the contact area between the user and the electrode 22b is very small, there is a possibility that the heat is locally generated on the skin of the user.

In the high-frequency cosmetic treatment apparatus 2, by changing the intensity of the voltage applied to the electrode 22b, the center electrode 230, and the like, in accordance with the outputs of the photosensor 223a and the photosensor 223b, it is possible to prevent the skin of the user from being locally heated.

REGARDING MODIFIED EXAMPLES

Although the first and second embodiments are concretely described above, the present invention is not limited only to the embodiments, and can be changed in various ways without departing from the scope of the present invention. Hereinafter, various modified examples of the present invention will be described. In the following description, parts corresponding to those of the first and second embodiments are denoted by the same reference numerals, and detailed description thereof will be omitted.

Modified Example 1

Figure 9:
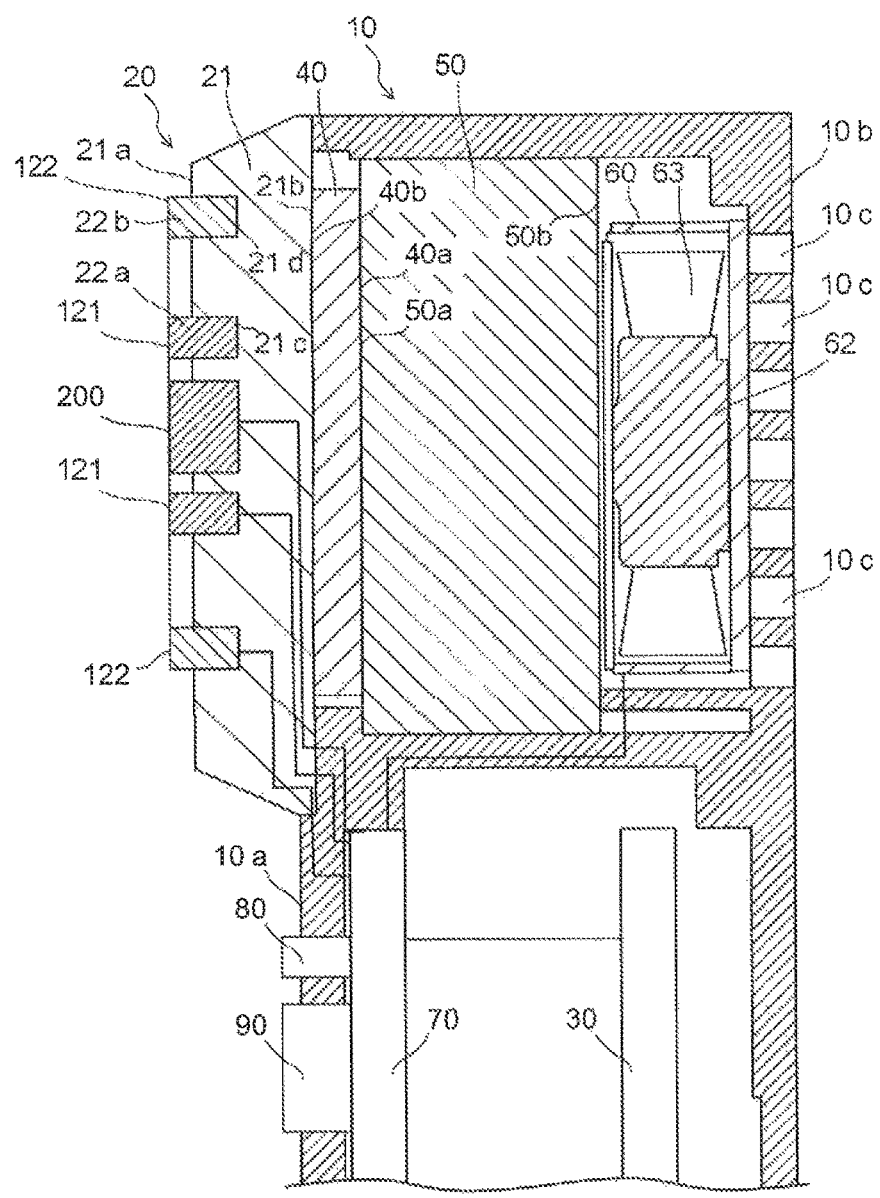
FIG. 9 is a partial sectional view illustrating a modified example of the high-frequency cosmetic treatment apparatus 1.

It is also possible to provide a touch sensor 200 to the electrode base 21, as illustrated in FIG. 9. The touch sensor 200 detects the contact of the pair of electrodes 22a and 22b with respect to the skin surface of the user. In response to the detection of the contact of the pair of electrodes 22a and 22b detected by the touch sensor 200, the high-frequency voltage is applied to the pair of electrodes 22a and 22b. Further, when the touch sensor 200 does not detect the contact of the pair of electrodes 22a and 22b with respect to the skin surface of the user, the high-frequency voltage is not applied to the pair of electrodes 22a and 22b.

Consequently, after the pair of electrodes 22a and 22b is brought into contact with the skin surface of the user, the high-frequency voltage is applied to the pair of electrodes 22a and 22b.

When the high-frequency voltage is applied to the pair of electrodes 22a and 22b before the pair of electrodes 22a and 22b is brought into contact with the skin surface of the user, since the electrodes 22a and 22b are brought into contact with body hair and the like, the high-frequency current sometimes flows through the skin surface of the user from the pair of electrodes 22a and 22b in a quite small contact area.

In this case, the user often feels uncomfortableness such as tingling sensation.

By applying the high-frequency voltage to the pair of electrodes 22a and 22b after the pair of electrodes 22a and 22b is brought into contact with the skin surface of the user, it is possible to make the high-frequency current flow through the skin surface of the user in a wide contact area. As a result of this, it is possible to prevent the user from feeling uncomfortableness.

As the touch sensor 200, it is possible to employ a touch sensor of various types such as a resistance film type, an electrostatic capacitance type, an acoustic wave type, an infrared detection type, and a mechanical type. Further, it is also possible that an acceleration sensor is provided, instead of the touch sensor 200. For example, when the acceleration sensor detects that the high-frequency cosmetic treatment apparatus 1 is moved, the high-frequency voltage is applied to the pair of electrodes 22a and 22b.

Modified Example 2

Figure 10:
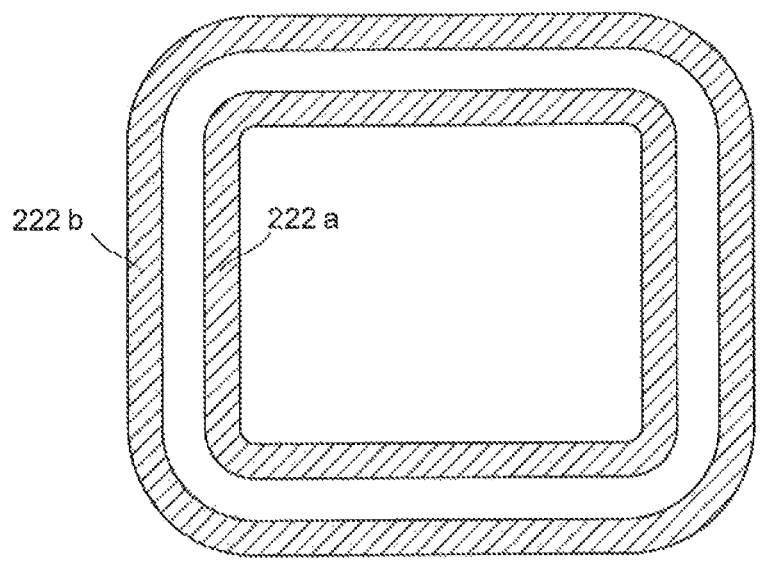
FIG. 10 is a schematic view illustrating a modified example of the electrode 22a and the electrode 22b.
Figure 11:
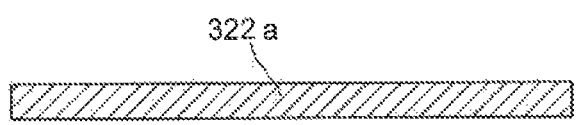
FIG. 11 is a schematic view illustrating a modified example of the electrode 22a and the electrode 22b.
Figure 11:
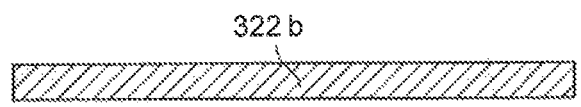
Figure 12:
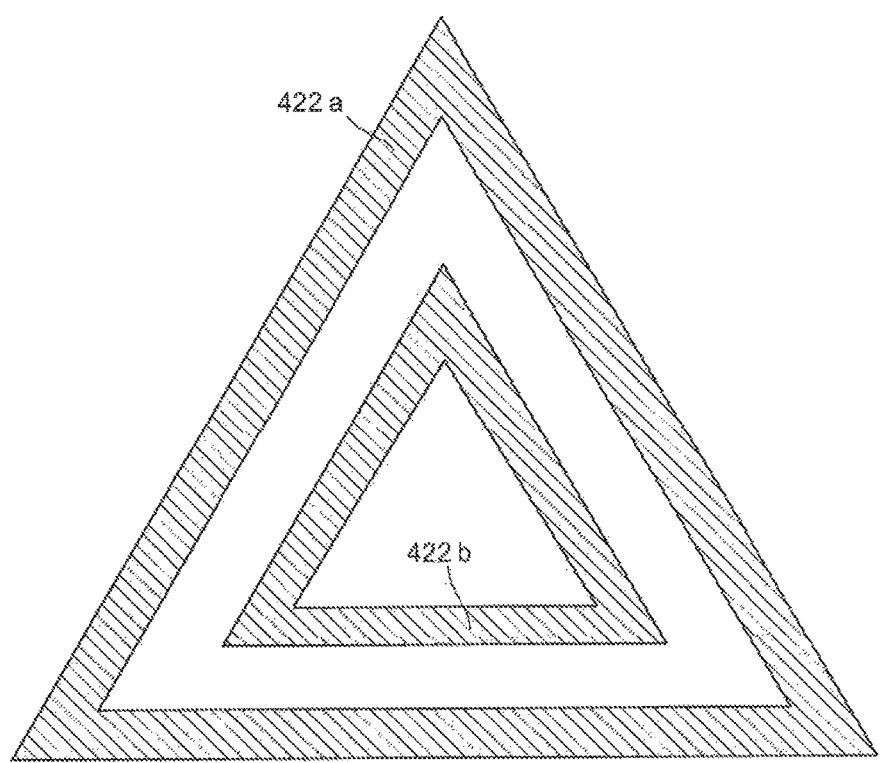
FIG. 12 is a schematic view illustrating a modified example of the electrode 22a and the electrode 22b.

Although each of the pair of electrodes 22a and 22b is formed in the circular ring shape in the first and second embodiments, and the modified example 1, it is also possible to design such that each of the pair of electrodes is formed in an approximately angular ring shape, as each of a pair of electrodes 222a and 222b illustrated in FIG. 10, the pair of electrodes is formed by arranging bar-shaped electrodes to be parallel to each other, as a pair of parallel electrodes 322a and 322b illustrated in FIG. 11, or each of the pair of electrodes is formed in an approximately triangular shape, as each of a pair of parallel electrodes 422a and 422b illustrated in FIG. 12, for example. The shape of each of the pair of electrodes 22a and 22b may also be an approximately perfect circular shape, or it may also be an elliptical shape.

Modified Example 3

As another modified example, it is also possible to configure such that a pair of ion introducing electrodes is provided to a predetermined place of the main body 10 or the electrode head 20, for example, so that treatment with the use of an ion introduction method or an ion lead-out method can be conducted. For example, it is also possible to configure such that one of the pair of ion introducing electrodes is arranged between the electrodes 22a and 22b in pairs, and the other ion introducing electrode is provided on the front surface part 10a of the main body 10.

Modified Example 4

It is also possible to provide a switch for switching a forward direction and a reverse direction of the current which flows through the Peltier element.

Modified Example 5

Figure 13:
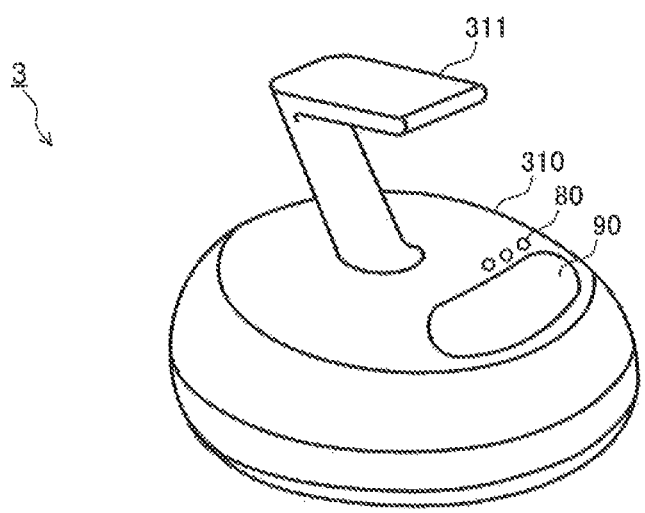
FIG. 13 is a schematic view illustrating another modified example.

The shape of the main body 10 or the main body 210 can be appropriately changed. For example, the shape may also be a shape such as one in a high-frequency cosmetic treatment apparatus 3 illustrated in FIG. 13. FIG. 13 is a schematic view illustrating another modified example of the main body 10 or the main body 210.

The high-frequency cosmetic treatment apparatus 3 includes a main body 310 having a handling part 311 held by a hand of the user, on an upper surface side thereof.

The main body 310 has a shape similar to a shape of sphere crushed from up and down directions. On the upper surface of the main body 310, the operation button 80 and the display part 90 can be disposed. The pair of electrodes 22a and 22b, and the like, is disposed on a lower surface of the main body 310.

Other Modified Examples

It is also possible to configure such that the partial configurations exemplified in the first and second embodiments, and the modified example 1 to the modified example 5 described above are appropriately combined, or a specific configuration is excluded.

For example, the respective elements in the first and second embodiments may also be excluded.

For example, it is also possible that the RF driver 271a is not provided.

For example, it is also possible that the electrode 22a, the electrode 22b, the photosensor 223a, the photosensor 223b, or the like is not provided. When the electrode 22a is not provided, the photosensor 223a and the photosensor 223b are arranged between the electrode 22b and the center electrode 230.

The positions at which the operation button 80, the display part 90, and the like are disposed, are not limited in particular. It is also possible to form the electrode 22a or the like in an elliptical shape. It is also possible to form the center electrode 230 in a circular ring shape.

What is claimed is:

1. A high-frequency cosmetic treatment apparatus, comprising:
   a portable casing having a head;
   a base made of an insulating material and disposed on the head;
   a first electrode and a second electrode to be contacted with a skin of a user, each of the first electrode and the second electrode protruding from the base; and
   a first power supply disposed in the casing, and to supply a high-frequency current between the first and second electrodes, wherein:
the first electrode and the second electrode are separated from each other,
the first electrode has a first ring shape;
the second electrode has a second ring shape and is inside the first electrode;
a part of the base is disposed between the first and second electrodes;
the first electrode includes:
a first top face having an annular shape and configured to contact with the skin,
a first bottom face opposite to the first top face, and
an inner side connecting the first top face and the first bottom face; the second electrode includes:
a second top face having an annular shape and configured to contact with the skin corresponding to the first top face,
a second bottom face opposite to the second top face, and
an outer side connecting the second top face and the second bottom face and facing the inner side of the first electrode;
at least a part of the inner side, at least a part of the outer side, the first top face, and the second top face protrude from the base in a direction from the first bottom face toward the first top face; and
the part of the inner side and the part of the outer side are separated from each other and directly face each other above the base.

2. The high-frequency cosmetic treatment apparatus according to claim 1, further comprising:
a heat sink disposed in the head of the casing;
a Peltier element disposed on the heat sink and in the casing; and
a second power supply to supply a drive current to the Peltier element, wherein the first and the second electrodes are disposed on the heat sink via the Peltier element.

3. The high-frequency cosmetic treatment apparatus according to claim 1, wherein:
the first electrode has a first diameter, and the second electrode has a second diameter smaller than the first diameter;
the cosmetic treatment apparatus further comprises a third electrode with a columnar shape, having a third diameter smaller than the second diameter, and having a peripheral edge disposed inside the second electrode; and
the first power supply further supplies a current of a second frequency between the first and third electrodes, or between the second and third electrodes.

4. The high-frequency cosmetic treatment apparatus according to claim 3, further comprising:
an ultrasonic vibrator to vibrate the third electrode;
a second power supply to supply electric power to the ultrasonic vibrator; and
a vibration controller to control the supply of the electric power to the ultrasonic vibrator.

5. The high-frequency cosmetic treatment apparatus according to claim 3, further comprising:
a first and a second contact sensors to detect contact between the first and second electrodes and a skin surface of the user,
wherein the first power supply changes power of the high-frequency current or the current of the second frequency in response to the detection of the contact of the skin surface detected by the first and/or second contact sensor.

6. The high-frequency cosmetic treatment apparatus according to claim 1, further comprising:
a current sensor to detect a value of the high-frequency current flowing through the first and second electrodes,
wherein the first power supply does not supply the high-frequency current to the first and second electrodes or reduces power of the high-frequency current, when the value of the high-frequency current detected by the current sensor is equal to or greater than a threshold value.

7. The high-frequency cosmetic treatment apparatus according to claim 1, further comprising:
a contact sensor to detect contact between the first and second electrodes and a skin surface of the user,
wherein the first power supply supplies the high-frequency current to the first and second electrodes in response to the detection of the contact between the first and second electrodes and the skin surface detected by the contact sensor.

8. The high-frequency cosmetic treatment apparatus of claim 1, wherein:
the first top face has a circular inner edge with a first radius,
the second top face has a circular outer edge with a second radius, and
the circular outer edge and the circular inner edge have a common center and are parallel to each other.

9. The high-frequency cosmetic treatment apparatus of claim 1, wherein:
the outer side has:
a plurality of first areas being away from each other and along a circumferential direction of the outer side, and
a plurality of second areas disposed between the first areas; and the inner side has:
a plurality of third areas being away from each other and along a circumferential direction of the inner side, and
a plurality of fourth areas disposed between the first areas.

10. The high-frequency cosmetic treatment apparatus of claim 9, wherein:
the first and third areas face each other and are parallel to each other, and
the second and fourth areas face each other but are not parallel to each other.

11. The high-frequency cosmetic treatment apparatus of claim 9, wherein:
the first and third areas face each other and have a first radius of curvature, and
the second and fourth areas face each other and have a second radius of curvature different from the first radius of curvature.

* * * * *